United States Patent [19]
Burns et al.

[11] Patent Number: 5,854,073
[45] Date of Patent: Dec. 29, 1998

[54] STABILIZATION OF BILIRUBIN IN CONTROL SERA AND CALIBRATORS

[75] Inventors: Geoffrey Burns, Marple, Great Britain; Martina Junius-Comer, Tutzing, Germany

[73] Assignee: Bohringer Mannheim GmbH, Mannheim, Germany

[21] Appl. No.: 822,950

[22] Filed: Mar. 21, 1997

[30] Foreign Application Priority Data

Mar. 22, 1996 [DE] Germany .......................... 196 11 458.6
Jun. 15, 1996 [DE] Germany .......................... 196 23 955.9

[51] Int. Cl.⁶ .................................................. G01N 31/00
[52] U.S. Cl. ................................... 436/12; 436/8; 436/16; 436/97; 436/176; 422/61; 428/528
[58] Field of Search ................................ 436/8, 12, 16, 436/18, 63, 97, 106, 124, 127, 131, 140, 176; 422/61; 252/408.1; 424/528

[56] References Cited

U.S. PATENT DOCUMENTS

| | | | |
|---|---|---|---|
| 4,220,713 | 9/1980 | Rittersdorf et al. | 435/14 |
| 4,288,343 | 9/1981 | Louderback | 436/12 |
| 4,571,383 | 2/1986 | Takayama et al. | 435/25 |
| 5,278,073 | 1/1994 | Grandjean | 436/12 |
| 5,281,536 | 1/1994 | Wild et al. | 436/16 |
| 5,296,377 | 3/1994 | Rapkin et al. | 436/13 |
| 5,401,639 | 3/1995 | Saldivar, Jr. et al. | 435/14 |

*Primary Examiner*—Maureen M. Wallenhorst
*Attorney, Agent, or Firm*—Nikaido Marmelstein Murray & Oram, LLP

[57] ABSTRACT

The invention concerns a stable control serum or calibration serum containing bilirubin to analytically examine the methodical accuracy of individual parameters in human sera or patients. The control serum or calibration serum according to the invention is used to stabilize bilirubin in solutions and to generally increase the stability of control sera or calibration sera.

13 Claims, No Drawings

STABILIZATION OF BILIRUBIN IN CONTROL SERA AND CALIBRATORS

The invention concerns a stable control or calibration serum containing bilirubin.

Control liquids with a serum-like composition which contain the parameters to be determined in known, exactly defined concentrations are used to analytically examine the methodical accuracy of individual parameters in human sera of patients. One differentiates between special control sera and calibration sera which respectively serve to control or calibrate specific parameters and so-called universal control sera and calibration sera which can be used to control or to calibrate respectively as many as possible of the common parameters by all methods of determination which are usually carried out in practice.

The requirements that are made for such products in clinical chemistry routine operation include:
- an exactly known concentration of the measured parameters has to be adhered to;
- the concentrations have to be within the medically relevant measuring range (normal and pathological);
- the control sera and calibration sera must be easy to handle;
- the control sera and calibration sera must have the longest possible stability.

If the control serum or calibration serum is used on automated analysers high standards have to be set especially for the latter two items (handling and stability). A parameter which is critical with regard to stability but important for clinical chemistry is the substance bilirubin which is very sensitive to light and oxidizing agents. Bilirubin is measured for the diagnosis, differential diagnosis and monitoring of icterus. Whereas in freshly prepared sera of human or animal origin or in lyophilisates the biliburin concentration—if the action of light is excluded—remains constant for a relatively long time even at temperatures of about 25° C., this substance is rapidly degraded and thus its concentration changes in serum pools or in sera stored for a longer period even at temperatures of about 4° C. If calibration sera were to be used with a reduced measurable concentration of bilirubin, this would lead to false bilirubin values in the serum samples of patients and thus lead to changes in therapy decisions.

The oxidation of bilirubin can be slowed down by addition of sulfhydryl components such as dithiothreitol or cysteine (Trivin F., Odievre M., Lemonnier A. (1977) Clin. Chem. 23, 541–545). In U.S. Pat. No. 4,201,694 the stabilization of conjugated bilirubin in blood serum is described by adding a sulfhydryl component at a pH of 8.2–9.2. Reducing agents such as ascorbic acid (Watson D. (1962) Clin. Sci. 22, 435–445) also counteract the oxidative degradation of bilirubin.

The stabilization of bilirubin by using an oxygen-labile reagent, glucose, glucose oxidase, a hydrogen donor, sterile membrane fragments of bacteria and a reagent-binding agent is achieved in WO 92/07088. However, this process is obviously too time consuming, too complicated and too expensive to ensure its industrial utility. The stabilization of bilirubin by polyols at high concentrations such as ethylene glycol has also been described (Louderback, A., Jendrzejezak B., Doumas B. T., Foley Th., (1980) Fresenius Z. Anal. Chem. 301, 145). The control sera and calibration sera can become viscous by the addition of such high concentrations of polyols. This can lead to difficulties and inaccuracies in the pumping and pipetting steps of automated analysis which is why it is not expedient to add high concentrations of polyols. It is also known that metal ions accelerate the oxidative degradation process of bilirubin whereas the concurrent presence of metal ion complexing reagents such as EDTA delays the autooxidation (Fog J., Bakken A. F. (1967) Scand. J. Clin. Lab. Invest. 20, 70–72; Fog J., Bugge-Asperheim (1964) Nature 203, 756–757; De Ewenson I. W., Gianturco F. A., Gramaccioni P. (1966) Experimentia XXII, 14–15; U.S. Pat. No. 4,344,864).

The major disadvantage of all the above-mentioned methods is the necessity to use high concentrations of the aforementioned reagents. Thus a stabilizer for a particular parameter can often interfere with the determination of other parameters. For example reducing SH compounds can interfere with a subsequent enzymatic reaction. The adverse effect on PAP tests such as creatinine PAP or uric acid PAP is particularly critical. The PAP test comprises an indicator reaction in which $H_2O_2$ reacts with phenol aminophenazone (PAP) to form a red dye the absorption of which is proportional to the creatinine/uric acid concentration.

When manufacturing universal control sera and calibration sera it is therefore advantageous to use as little as possible of the additives. The object of the invention was to provide a control serum and calibration serum which contains bilirubin in a stabilized form whose concentration is in the medically relevant measuring range, whose handling is simple and which has a long stability. The object is achieved by the invention which is characterized in more detail in the claims which essentially consists of the stabilization of bilirubin in control sera and calibration sera. This includes the chemical compounds characterized in more detail in the claims, the use thereof, processes for their production as well as methods for the detection of bilirubin which protect bilirubin and do not interfere with other tests in particular the PAP test.

The invention concerns a bilirubin-containing control serum or calibration serum which contains a chemical compound of the general formula (I):

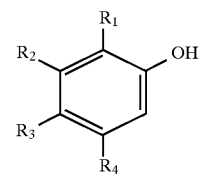

in which
- R1=denotes H, OH, an alkyl residue with 1–8 C atoms, COOR5 or SO₃R5
- R2=denotes H, OH, an alkyl residue with 1–8 C atois, COOR5 or SO₃R5
- R3=denotes H or OH
- R4=denotes H, COOR5, COR5 or SO₃R5
- R5=denotes H or an alkyl residue with 1 to 6 C atoms and/or a chemical compound of the general formula (II)

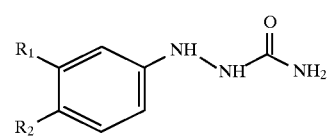

in which
- R1=denotes H, halogen: Cl, Br, F or alkyl: 1–6 C atoms
- R2=denotes H, alkyl: C1–C6 or alkoxy: 1–6 C atoms.

For example compounds of formula (I) are particularly preferred in which:

R1=OH; R2=OH; R3=H; R4=COOC$_3$H$_7$ (=Progailin®) and

R1=OH; R2=H; R3=OH; R4=COC$_4$H$_9$ (=2,4,5-trihydroxybutyrophenone)

and the compound of formula (II) in which:

R1=H; R2=CH$_3$ (=1-(4-methylphenyl)-semicarbazide).

The compounds of the general formula (I) and (II) are used in the control serum and calibration serum at a concentration of 0.001 to 1.5 mmol/l preferably of 0.001 to 0.1 mmol/l (Progalling®) or 0.01 to 1.5 mmol/l (1-(4-metlaoxyphenyl)-semicarbazide, 2,4,5-trihydroxybutyropheinone, 1-(4-methylphenyl)-semicarbazide, 1-phenylsemiscarbazide and 1-(3-chlorophenyl)-semicarbazide.

It is particularly preferable to use the compounds of the general formula (I) or (II) at a concentration of 0.03 to 0.05 mmol/l (Progallin®), 0.03 to 0.25 mmol/l (1-(4-methoxyphenyl)-semicarbazide) 0.05 to 0.25 mmol/l (1-(4-methylphenyl)-semicarbazide), 0.15 to 0.25 mmol/l (2,4,5-trihydroxybutyrophenone and 1-phenylsemicarbazide) or 0.15 to 0.3 mmol/l (1-(3-chlorophenyl)-semicarbazide).

The stabilizing effect on the bilirubin present in the control serum or calibration serum does not occur until the stabilizer and the control serum or calibration serum containing the bilirubin are present together in a solution. The stabilizer and the control serum and calibration serum can be stored as follows:

control or calibration serum and stabilizer together in a lqophilized form or control or calibration serum and stabilizer separate in lyophilized form or control or calibration serum lyophilized, stabilizer in a liquid form or control or calibration serum and stabilizer together in a liquid form.

In order to achieve an additional stabilizing effect the control or calibration serum and the stabilizer can be stored at low temperatures and optionally below freezing point.

The control or calibration serum according to the invention can contain additional auxiliary substances in addition to the analyte parameters such as further analyte stabilizers, detergents and preservatives. When these auxiliary substances are added care must be taken in each case that they do not interfere with the measurement of particular parameters.

A particularly high stability of bilirubin is achieved by storing the reagent under a protective gas atmosphere especially an N$_2$ protective gas atmosphere. The protective gas atmosphere has a very beneficial effect on the stability of other parameters such as uric acid in addition to the stability of bilirubin. The bicarbonate value is stabilized by the addition of ca. 0.3 vol. % CO$_2$ to the N$_2$ inert gas. In addition to this analyte stabilizer it is also possible to add further individual analyte stabilizing auxiliary substances. Thus, for example addition of EDTA stabilizes the iron value. The addition of a dilute Fe solution during the production of the control serum or calibration serum in the presence of EDTA preferably in a ratio of 1:1.1 (Fe/EDTA) results in stabilized Fe complexes which are not destroyed by lipoproteins or bovine serum albumin.

The addition of creatine has a positive effect on the stability of the parameter creatinine since this prevents or at least strongly reduces the creatinine hydrolysis.

In previous conventional control sera and calibration sera an egg-yolk fraction has been used for the triglyceride parameter. Turbidities may occur with such a composition. The substitution of this egg-yolk fraction by glycerol as the triglyceride can completely avoid this potential interference. Glycerol exhibits no tendency to form turbidity even after a longer storage and is therefore suitable for use in the control serum or calibration serum according to the invention.

The pH value of the control serum or calibration serum is adjusted to a pH of preferably 6.0 to 8.6 by using a buffer.

The control serum and calibration serum according to the invention is stable in the unopened state for 12 months at 4° C. This stability can be considerably increased by storage at −20° C. Even in the opened state at 10° C. the product is stable for several days. It is excellently suitable as a quality control serum and calibration serum for parameters in clinical diagnostics especially with regard to bilirubin. The control or calibration serum according to the invention is particularly preferably used for automated clinical diagnostics.

A further subject matter is a process for the production of a control or calibration serum starting with a bovine serum albumin solution which is mixed with the desired parameters up to the desired parameter concentration wherein the stated and optionally other auxiliary agents are added.

A further subject matter is the use of the compounds of the general formulae (I) and/or (II) to stabilize bilirubin in solutions.

A further subject matter is a method to increase the storage stability of calibration sera and control sera containing bilirubin which is achieved by adding compounds of the general formulae (I) and/or (II) to stabilize bilirubin in solutions.

A further subject matter of the invention is a method for the detection of bilirubin which is characterized by measuring the bilirubin content of the sample, measuring bilirubin in a control serum or calibration serum according to the invention and subsequently determining the bilirubin content of the sample by comparing the two measurements. The bilirubin determination in the sample or in the control or calibration serum is carried out according to methods known to a person skilled in the art.

The invention also concerns a kit for measuring bilirubin in samples which contains the control serum and calibration serum according to the invention and which additionally contains the reagents necessary for the measurement.

The invention is elucidated in more detail by the following examples:

EXAMPLE 1

Stabilization of bilirubin in control sera

In order to examine the stability of bilirubin a Progallin®-free PPU (Precipath U: Universal control serum with target values in the pathological range; Boehringer Mannheim GmbH, Cat. No. 171 760) is supplemented with the stabilizers. A first screening is carried out with various concentrations of stabilizers. The samples are stored in the dark and subsequently D-biLirubin and T-bilirubin stabilities are measured after 4 hours at 25° C. (D-bilirubin also referred to as δ-bilirubin or Bd is bound covalently to albumin and therefore has a half-life of ca. 18 days. T-bilirubin stands for total bilirubin—conjugated and non-conjugated). The D-bilirubin and T-bilirubin were measured with the appropriate test kits of Boehringer Mannheim GmbH, Germany:

T-bilirubin: Cat. No. 104 0804, lot 64430201 (HiCo, DPD) method)

D-bilirubin: Cat. No. 110 9774, lot 64548901 (Jendrassik method)

Table 1 shows the results of the screening.

TABLE 1

| | Concentration (mmol/l) | % recovery D-bilirubin (after 4 h/25° C.) | % recovery T-bilirubin (after 4 h/25° C.) |
|---|---|---|---|
| No addition | — | 74.5 | 79.9 |
| Progallin ® | 0.3 | 100.2 | 97.3 |

TABLE 1-continued

| | Concentration (mmol/l) | % recovery D-bilirubin (after 4 h/25° C.) | % recovery T-bilirubin (after 4 h/25° C.) |
|---|---|---|---|
| | 0.03 | 96.7 | 95.1 |
| | 0.01 | 89.5 | 88.0 |
| 2,4,5-trihydroxy-butyrophenone | 0.3 | 98.2 | 102.6 |
| | 0.03 | 76.3 | 80.6 |
| | 0.01 | 73.8 | 78.3 |
| no addition | — | 63.2 | 76.5 |
| 1-(4-methyl-phenyl)-semi-carbazide | 0.3 | 93.6 | 97.2 |
| | 0.03 | 77.1 | 84.5 |
| | 0.01 | 68.7 | 78.8 |
| 1-(3-chloro-phenyl)-semi-carbazide | 0.3 | 88.4 | 91.3 |
| | 0.03 | 73.5 | 82.0 |
| | 0.01 | 67.1 | 78.1 |
| 1-phenylsemi-carbazide | 0.3 | 88.3 | 91.8 |
| | 0.03 | 70.7 | 80.0 |
| | 0.01 | 66.0 | 77.9 |
| 1-(4-methoxy-phenyl)-semi-carbazide | 0.3 | 97.7 | 101.1 |
| | 0.03 | 82.6 | 89.6 |
| | 0.01 | 68.9 | 79.6 |

The claimed substances have a positive influence on the stability of D-bilirubin and T-bilirubin.

Tables 1 and 2 show the results of a fine optimization of the concentrations of these substances. The recovery of D bilirubin (after 4 hours at 25° C.) and uric acid is shown in relation to the concentration of the appropriate stabilizers. The substances used according to the invention stabilize bilirubin.

EXAMPLE 2

Interferences in the creatinine-PAP/uric acid-PAP test

Also in this case various concentrations of the claimed substances according to Table 2 were used.

The samples were again stored in the dark. However, the interferences in the uric acid-PAP and creatinine-PAP test were only measured once at the beginning of the experiment. The corresponding test kits from Boehringer Mannheim GmbH, Germany were used for the determinations of uric acid and creatinine PAP and carried out according to the instructions of the manufacturer of the tests.

Uric acid-PAP: Cat. No. 144 6765, lot 64834001 and creatinine-PATP: Cat. No. 148 9291, lot 64720101

TABLE 2

| | Concentration (mmol/l) | % recovery uric acid | % recovery creatinine |
|---|---|---|---|
| No addition | — | 100.0 | 79.9 |
| Progallin ® | 0.3 | 15.2 | 91.2 |
| | 0.03 | 87.0 | 96.9 |
| | 0.01 | 94.6 | 97.8 |
| 2,4,5-trihydroxy-butyrophenone | 0.3 | 89.9 | 92.9 |
| | 0.03 | 99.6 | 97.6 |
| | 0.01 | 100.1 | 98.1 |
| no addition | — | 100.0 | 100.1 |
| 1-(4-methyl-phenyl)-semi-carbazide | 0.3 | 90.3 | 96.7 |
| | 0.03 | 97.0 | 98.9 |
| | 0.01 | 96.6 | 101.5 |
| 1-(3-chloro-phenyl)-semi-carbazide | 0.3 | 96.4 | 97.8 |
| | 0.03 | 97.9 | 100.0 |
| | 0.01 | 98.0 | 99.6 |
| 1-phenylsemi-carbazide | 0.3 | 97.3 | 98.5 |
| | 0.03 | 99.4 | 99.6 |
| | 0.01 | 99.0 | 100.7 |
| 1-(4-methoxy-phenyl)-semi-carbazide | 0.3 | 78.1 | 82.5 |
| | 0.03 | 98.0 | 98.2 |
| | 0.01 | 98.9 | 99.6 |

The claimed substances have different effects on uric acid PAP whereas the effects on creatinine PAP are uniform.

Using the results shown it is possible to establish an optimal concentration for the stabilizers which guarantees a high stability of bilirubin and a low interference of the PAP tests:

| | |
|---|---|
| Progallin ® | 0.001–0.1 mmol/l |
| 2,4,5-trihydroxybutyrophenone | 0.01–1.5 mmol/l |
| 1-(4-methylphenyl)-semicarbazide | 0.01–1.5 mmol/l |
| 1-phenylsemicarbazide | 0.01–1.5 mmol/l |
| 1-(3-chlorophenyl)-semicarbazide | 0.01–1.5 mmol/l |
| 1-(4-methoxyphenyl)-semicarbazide | 0.01–1.5 mmol/l | particularly preferred are:

| | |
|---|---|
| Progallin ® | 0.03–0.05 mmol/l |
| 2,4,5-trihydroxybutyrophenone | 0.15–0.25 mmol/l |
| 1-(4-methylphenyl)-semicarbazide | 0.05–0.25 mmol/l |
| 1-phenylsemicarbazide | 0.15–0.25 mmol/l |
| 1-(3-chlorophenyl)-semicarbazide | 0.15–0.30 mmol/l |
| 1-(4-methoxyphenyl)-semicarbazide | 0.03–0.25 mmol/l |

Consequently it can be demonstrated that the claimed substances when optimized accordingly can be used as bilirubin stabilizers as well as non-interfering substances in the creatinine-PAP and uric acid-PAP.

In the case of calibration sera or control sera containing bilirubin which have a different composition than that of the serum used in examples 1 and 2 preferred concentration ranges may result which differ slightly from the ranges stated here. A person skilled in the art can easily determine the preferred concentrations in each case on the basis of simple investigations as shown in examples 1 and 2.

We claim:

1. Control serum or calibration serum comprising bilirubin and a stabilizer comprising at least one compound selected from the group consisting of:

a compound of formula (I):

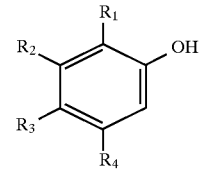

wherein
$R_1$ is H, OH, $C_{1-8}$ alkyl, $COOR_5$ or $SO_3R_5$;
$R_2$ is H, OH, $C_{1-8}$ alkyl, $COOR_5$ or $SO_3R_5$;
$R_3$ is H or OH;
$R_4$ is H, $COOR_5$, $COR_5$ or $SO_3R_5$
$R_5$ is H or $C_{1-6}$ alkyl;
and a compound of formula (II)

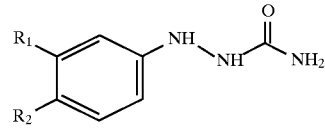

wherein
$R_1$ is H, Halogen or $C_{1-6}$ alkyl;
$R_2$ is H, $C_6$ alkyl, or $C_{1-6}$ alkoxy.

2. The control serum or calibration serum of claim 1 wherein the stabilizer comprises a compound of formula II, wherein the halogen is selected from the group consisting of Cl, Br, and F.

3. The control serum or calibration serum of claim 1 wherein the stabilizer comprises a compound of formula (1)

wherein $R_1$ is OH, $R_2$ is OH, $R_3$ is H, and $R_4$ is COOC$_3$H$_7$; or wherein $R_1$ is OH, $R_2$ is H, $R_3$ is OH, and $R_4$ is COC$_4$H$_9$(2,4,5-trithydroxybutyrophenone).

4. The control serum or calibration serum of claim 1, wherein the stabilizer comprises a compound of formula II, wherein the compound of formula (II) is a compound wherein $R_1$ is H and $R_2$ is CH$_3$ (1-(4-methylphenyl)-semicarbazide).

5. The control serum or calibration serum of claim 1, further comprising preservatives or analyte stabilizers.

6. The control serum or calibration serum of claim 1 which is stored under protective gas.

7. The control serum or calibration serum claim 1, comprising 0.001 to 1.5 mmol/l of at least one compound of formula (I) or formula (II).

8. A method for measuring bilirubin comprising:
   a) measuring bilirubin in a sample,
   b) measuring bilirubin in the control serum or calibration serum according to claim 1,
   c) determining a content of bilirubin in said sample by comparing the measurement determined in step a) with the measurement determined in step b).

9. In a kit for measuring bilirubin in a biological sample, said kit containing reagents necessary for measuring bilirubin, the improvement comprising: a separate package containing the control serum or calibration serum containing bilirubin according to claim 1.

10. The control or calibration serum of claim 1, further comprising preservatives and analyte stabilizers.

11. The control or calibration serum of claim 1, comprising 0.001 to 1.5 mmol/l of at least one compound of formula (I) and formula (II).

12. A process for the stabilization of a control serum or calibration serum containing bilirubin, said process comprising adding at least one compound selected from the group consisting of: a compound of formula (I) and a compound of formula (II) to a control serum or calibration serum containing bilirubin, wherein a compound of formula (I) is

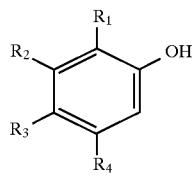

wherein
$R_1$ is H, OH, C$_{1-8}$ alkyl, COOR$_5$ or SO$_3$R$_5$;
$R_2$ is H, OH, C$_{1-8}$ alkyl, COOR$_5$ or SO$_3$R$_5$;
$R_3$ is or OH;
$R_4$ is H, COOR$_5$, COR$_5$ or SO$_3$R$_5$
$R_5$ is H or C$_{1-6}$, alkyl;
and a compound of formula (II) is

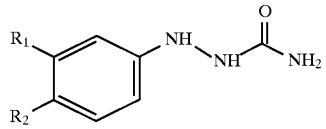

wherein
$R_1$ is H, Halogen or C$_{1-6}$ alkyl;
$R_2$ is H, C$_{1-6}$ alkyl, or C$_{1-6}$ alkoxy.

13. A method for increasing the storage stability of control sera or calibration sera comprising bilirubin, comprising adding at least one compound selected from the group consisting of a compound of formula (I) and a compound of formula (II) to the control sera or calibration sera, wherein a compound of formula (I) is

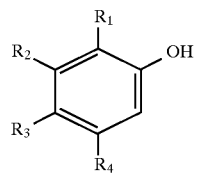

wherein
$R_1$ is H, OH, C$_{1-8}$ alkyl, COOR$_5$ or SO$_3$R$_5$;
$R_2$ is H, OH, C$_{1-8}$ alkyl, COOR$_5$ or SO$_3$R$_5$;
$R_3$ is H or OH;
$R_4$ is H, COOR$_5$, COR$_5$ or SO$_3$R$_5$
$R_5$ is H or C$_{1-6}$ alkyl;
and a compound of formula (II) is

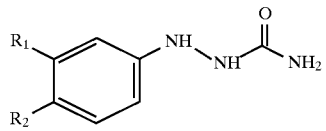

wherein
$R_1$ is H, Halogen or C$_{1-6}$ alkyl;
$R_2$ is H, C$_{1-6}$ alkyl, or C$_{1-6}$ alkoxy.

* * * * *